United States Patent
Ahmed et al.

(10) Patent No.: US 9,149,459 B2
(45) Date of Patent: Oct. 6, 2015

(54) SPHINGOSINE 1 PHOSPHATE RECEPTOR MODULATORS AND THEIR USE TO TREAT MUSCLE INFLAMMATION

(75) Inventors: Syed Sohail Ahmed, Siena (IT); Marco Londei, La Jolla, CA (US); Timothy Wright, Swampscott, MA (US); Peter Gergely, Oberwil (CH)

(73) Assignee: Novartis AG, Basel (CH)

( * ) Notice: Subject to any disclaimer, the term of this patent is extended or adjusted under 35 U.S.C. 154(b) by 306 days.

(21) Appl. No.: 13/055,206

(22) PCT Filed: Jul. 22, 2009

(86) PCT No.: PCT/EP2009/059440
§ 371 (c)(1),
(2), (4) Date: Jan. 21, 2011

(87) PCT Pub. No.: WO2010/010127
PCT Pub. Date: Jan. 28, 2010

(65) Prior Publication Data
US 2011/0124620 A1    May 26, 2011

(30) Foreign Application Priority Data
Jul. 23, 2008   (EP) .................................... 08161005

(51) Int. Cl.
A61K 31/497    (2006.01)
A01N 43/40     (2006.01)
A61K 31/44     (2006.01)
A61K 31/397    (2006.01)

(52) U.S. Cl.
CPC .................................... *A61K 31/397* (2013.01)

(58) Field of Classification Search
CPC .................................................... A61K 37/397
USPC ..................................................... 514/252.1
See application file for complete search history.

(56) References Cited

U.S. PATENT DOCUMENTS

| 7,825,150 | B2 | 11/2010 | Oravecz |
| 7,919,519 | B2 | 4/2011 | Burli |
| 8,101,775 | B2 | 1/2012 | Ahmed |
| 8,324,254 | B2 | 12/2012 | Ahmed |
| 2005/0033055 | A1 | 2/2005 | Bugianesi |

FOREIGN PATENT DOCUMENTS

| WO | WO 95/24383 A | 9/1995 |
| WO | WO 02/053159 A | 7/2002 |
| WO | WO 03/005965 A | 1/2003 |
| WO | WO 03/061567 A | 7/2003 |
| WO | WO 2004 087693 A | 10/2004 |
| WO | 2004103306 A2 | 12/2004 |
| WO | WO 2004/103306 A | 12/2004 |
| WO | WO 2005/000833 A | 1/2005 |
| WO | WO 2006047195 A2 * | 5/2006 |
| WO | WO 2006/058316 A | 6/2006 |
| WO | 2008021532 A2 | 2/2008 |
| WO | WO 2008/035239 A | 3/2008 |
| WO | WO 2010/072703 A1 | 7/2010 |

OTHER PUBLICATIONS

Dalakas et al. ("Polymyositis and dermatomyositis." The Lancet 362.9388 (2003): 971-982).*
Nazarpack-Kandlousy, Noureddin et al. "Regiochemical Tagging: A New Tool for structural characterization of Isomeric components in Combination Mixtures", J. Am. Chem. Soc., 2000, vol. 122; 3358-3366.
Jiang et al, 1993, New medicine, 24(5):233-234.
Ransohoff et al., 1983, "Impaired autologous mixed lymphocyte reaction with normal concanavalin A-induced suppression in adult polymyositis/dermatomyositis", Clin. Exp. ImmlDiol. (1983) 53:61-15.
Ogawa et al., 2007, "A novel sphingosine-1-phosphate receptor agonist KRP-203 attenuates rat autoimmune myocarditis", Biochemical and Biophysical Research Communications, 361:621-628.
Zanin et al., 2007, "Trophic action of sphingosine 1-phosphate in denervated rat soleus muscle", Am J Physiol. Cell Physiol., 294: C36-C46.

* cited by examiner

*Primary Examiner* — Layla Soroush
(74) *Attorney, Agent, or Firm* — James Lynch

(57) ABSTRACT

The use of an S1P receptor modulator of the formula (Ia) or (Ib) wherein the meaning of the different residues is that indicated in claim 14, in the preparation of a medicament for preventing, inhibiting or treating an inflammatory condition selected from polymyositis, dermatomyositis and nerve-muscle diseases e.g. muscular dystrophies and inclusion body myositis.

1 Claim, 1 Drawing Sheet

SPHINGOSINE 1 PHOSPHATE RECEPTOR MODULATORS AND THEIR USE TO TREAT MUSCLE INFLAMMATION

FIELD OF THE INVENTION

The present invention relates generally to specific sphingosine 1 phosphate (S1P) receptor modulators, and more specifically to their use to treat muscle inflammation such as polymyositis and other inflammatory conditions such as dermatomyositis and nerve-muscle diseases e.g. muscular dystrophies and inclusion body myositis.

BACKGROUND

Polymyositis is an immune-mediated disorder leading to an inflammation of the muscles. It results in weakness that can be severe. Polymyositis is a chronic illness with periods of increased symptoms, called flares or relapses, and minimal or no symptoms, known as remissions.

The therapy of such muscle inflammation diseases, and in particular polymyositis, is only partially effective, and in most cases only offers a short delay in disease progression despite anti-inflammatory and immunosuppressive treatment. Accordingly, there is a need for agents which are effective in the inhibition or treatment of muscle diseases, e.g. polymyositis, including reduction of, alleviation of, stabilization of or relief from the symptoms which affect the muscles.

SUMMARY OF THE INVENTION

In accordance with a first aspect of the invention, there is provided the use of an S1P receptor modulator of the formula Ia or Ib:

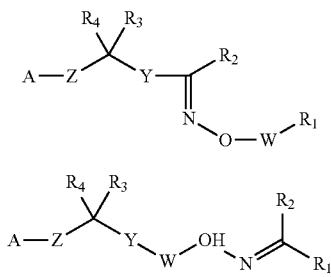

wherein

A is —C(O)OR$_5$, —OP(O)(OR$_5$)$_2$, —P(O)(OR$_5$)$_2$, —S(O)$_2$OR$_5$, —P(O)(R$_5$)OR$_5$ or 1H-tetrazol-5-yl, R$_5$ being H or C$_{1-6}$alkyl;

W is a bond, C$_{1-3}$alkylene or C$_{2-3}$alkenylene;

Y is C$_{6-10}$aryl or C$_{2-9}$heteroaryl e.g. C$_{3-9}$heteroaryl, optionally substituted by 1 to 3 radicals selected from halogen, —OH, —NO$_2$, C$_{1-6}$alkyl, C$_{1-6}$alkoxy; halo-substituted C$_{1-6}$alkyl and halo-substituted C$_{1-6}$alkoxy;

Z is chosen from:

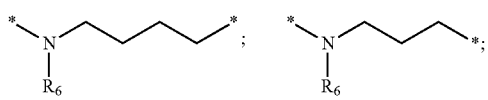

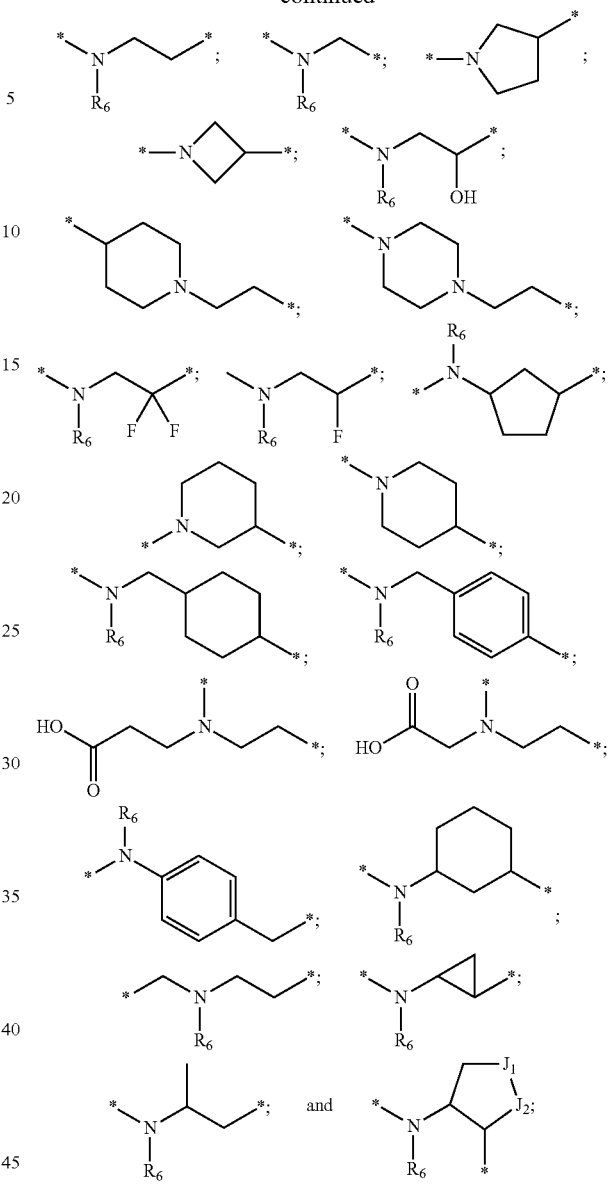

wherein the left and right asterisks of Z indicate the point of attachment between —C(R$_3$)(R$_4$)— and A of Formula Ia or Ib, respectively; R$_6$ is chosen from hydrogen and C$_{1-6}$alkyl; and J$_1$ and J$_2$ are independently methylene or a heteroatom chosen from S, O and NR$_5$; wherein R$_5$ is chosen from hydrogen and C$_{1-6}$alkyl; and any alkylene of Z can be further substituted by one to three radicals chosen from halo, hydroxy, C$_{1-6}$alkyl; or R$_6$ can be attached to a carbon atom of Y to form a 5-7 member ring e.g. a heterocyclic group as indicated in WO 04/103306A, e.g. azetidine;

R$_1$ is C$_{6-10}$aryl or C$_{2-9}$heteroaryl e.g C$_{3-9}$heteroaryl, optionally substituted by C$_{1-6}$alkyl, C$_{6-18}$aryl, C$_{6-10}$aryl C$_{1-4}$alkyl, C$_{3-9}$heteroaryl, C$_{3-9}$heteroarylC$_{1-4}$alkyl, C$_{3-8}$cycloalkyl, C$_{3-8}$cycloalkylC$_{1-4}$alkyl, C$_{3-8}$heterocycloalkyl or C$_{3-8}$heterocycloalkylC$_{1-4}$alkyl; wherein any aryl, heteroaryl, cycloalkyl or heterocycloalkyl of R$_1$ may be substituted by 1 to 5 groups selected from halogen, C$_{1-6}$alkyl, C$_{1-6}$alkoxy and halo substituted-C$_{1-6}$alkyl or -C$_{1-6}$alkoxy; and any alkyl group of $R_1$ can optionally have a methylene replaced by an atom or group chosen from —S—, —S(O)—, —S(O)$_2$—, —NR$_5$— and —O—; wherein R$_5$ is chosen from hydrogen or C$_{1-6}$alkyl;

$R_2$ is H, C$_{1-6}$alkyl, halo substituted C$_{1-6}$alkyl, C$_{2-6}$alkenyl or C$_{2-6}$alkynyl: and each of R$_3$ or R$_4$, independently, is H, halogen, OH, C$_{1-6}$alkyl, C$_{1-6}$alkoxy or halo substituted C$_{1-6}$alkyl or C$_{1-6}$alkoxy;

and the N-oxide derivatives thereof or prodrugs thereof, individual isomers and mixtures of isomers thereof; and the pharmacologically acceptable salts, solvates or hydrates thereof, in the preparation of a medicament for preventing, inhibiting or treating an inflammatory condition selected from polymyositis, dermatomyositis and nerve-muscle diseases e.g. muscular dystrophies and inclusion body myositis.

In accordance with a second aspect of the invention, there is provided an S1P receptor modulator as defined in the first aspect for use in preventing, inhibiting or treating an inflammatory condition selected from polymyositis, dermatomyositis and nerve-muscle diseases e.g. muscular dystrophies and inclusion body myositis.

In accordance with a third aspect of the invention, there is provided a method for preventing, inhibiting or treating an inflammatory condition such as polymyosisitis, dermatomyositis and nerve-muscle diseases e.g. muscular dystrophies and inclusion body myositis, in a subject in need thereof, comprising administering to said subject a therapeutically effective amount of an S1P receptor modulator as defined in the first aspect.

In accordance with a fourth aspect of the invention, there is provided a pharmaceutical composition comprising an S1P receptor modulator as defined in the first aspect for use in preventing, inhibiting or treating an inflammatory condition selected from polymyositis, dermatomyositis and nerve-muscle diseases e.g. muscular dystrophies and inclusion body myositis together with one or more pharmaceutically acceptable diluents or carriers therefor.

BRIEF DESCRIPTION OF THE FIGURES

FIG. 1(a) shows myotube diameter following exposure to DMSO (control); varying concentrations of compound A; and cytokine with varying concentrations of compound A.

FIG. 1(b) shows myotube diameter as a percentage of the control myotube diameter (exposed to the DMSO control) following exposure to varying concentrations of compound A; and cytokine with varying concentrations of compound A.

DETAILED DESCRIPTION OF THE INVENTION

Figure 1A:
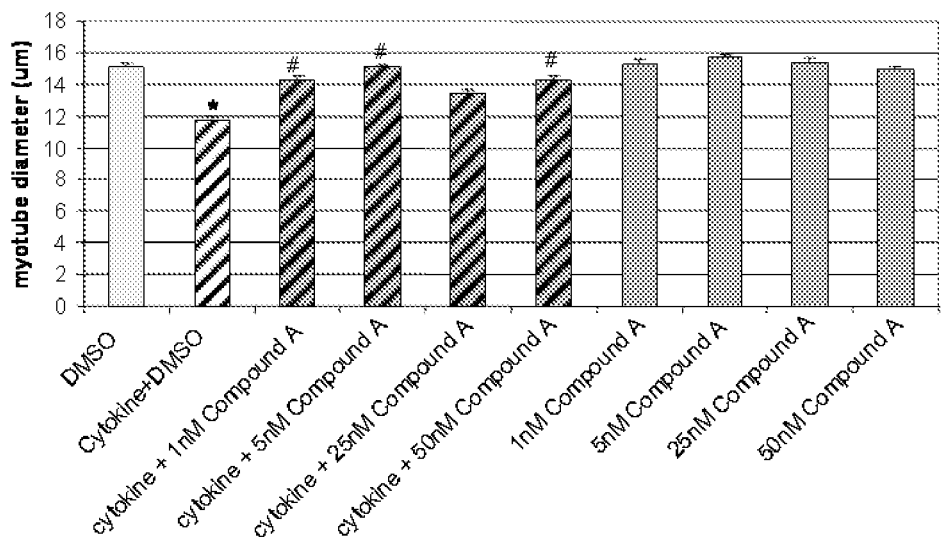
FIGS. 1(a) and 1(b) show the beneficial effects of the compounds of the invention on cytokine induced myotube atrophy.

S1P receptor modulators which can be used according to the invention are compounds of formula Ia or Ib, e.g. as disclosed in WO 04/103306A, WO 05/000833, WO 05/103309 or WO 05/113330, the contents of which are hereby incorporated by reference to the extent permitted by national law.

For example, the S1P receptor modulator may be a compound of formula Ia or Ib as defined below:

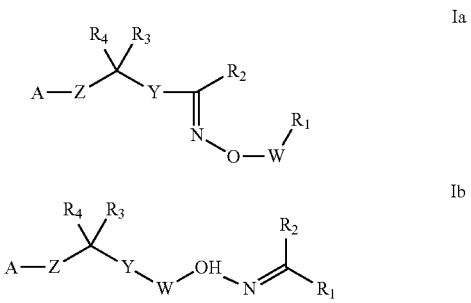

wherein

A is —C(O)OR$_5$, —OP(O)(OR$_5$)$_2$, —P(O)(OR$_5$)$_2$, —S(O)$_2$OR$_5$, —P(O)(R$_5$)OR$_5$ or 1H-tetrazol-5-yl, R$_5$ being H or C$_{1-6}$alkyl;

W is a bond, C$_{1-3}$alkylene or C$_{2-3}$alkenylene;

Y is C$_{6-10}$aryl or C$_{2-9}$heteroaryl e.g. C$_{3-9}$heteroaryl, optionally substituted by 1 to 3 radicals selected from halogen, —OH, —NO$_2$, C$_{1-6}$alkyl, C$_{1-6}$alkoxy; halo-substituted C$_{1-6}$alkyl and halo-substituted C$_{1-6}$alkoxy;

Z is chosen from:

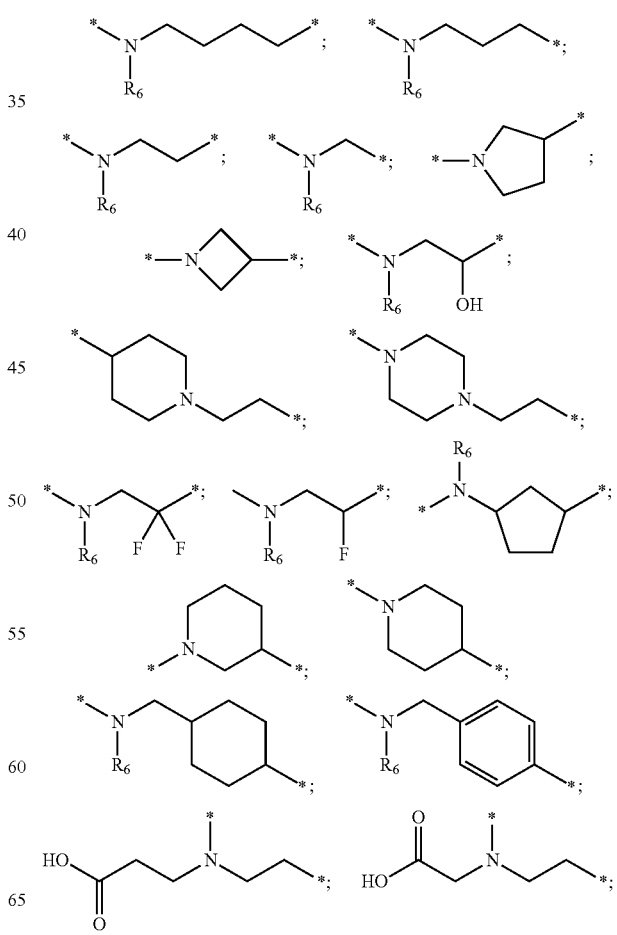

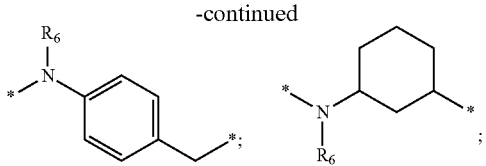

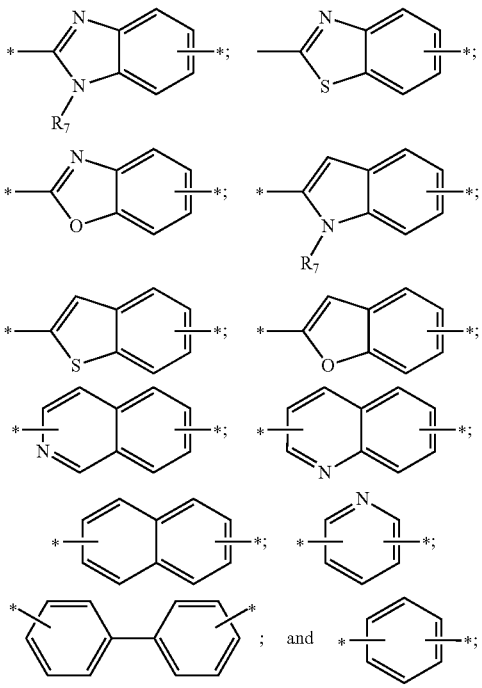

wherein the left and right asterisks of Z indicate the point of attachment between —C(R$_3$)(R$_4$)— and A of Formula Ia or Ib, respectively; R$_6$ is chosen from hydrogen and C$_{1-6}$alkyl; and J$_1$ and J$_2$ are independently methylene or a heteroatom chosen from S, O and NR$_5$; wherein R$_5$ is chosen from hydrogen and C$_{1-6}$alkyl; and any alkylene of Z can be further substituted by one to three radicals chosen from halo, hydroxy, C$_{1-6}$alkyl; or R$_6$ can be attached to a carbon atom of Y to form a 5-7 member ring e.g. a heterocyclic group as indicated in WO 04/103306A, e.g. azetidine;

R$_1$ is C$_{6-10}$aryl or C$_{2-9}$heteroaryl e.g C$_{3-9}$heteroaryl, optionally substituted by C$_{1-6}$alkyl, C$_{8-18}$aryl, C$_{6-10}$aryl C$_{1-4}$alkyl, C$_{3-9}$heteroaryl, C$_{3-9}$heteroarylC$_{1-4}$alkyl, C$_{3-8}$cycloalkyl, C$_{3-8}$cycloalkylC$_{1-4}$alkyl, C$_{3-8}$heterocycloalkyl or C$_{3-8}$heterocycloalkylC$_{1-4}$alkyl; wherein any aryl, heteroaryl, cycloalkyl or heterocycloalkyl of R$_1$ may be substituted by 1 to 5 groups selected from halogen, C$_{1-6}$alkyl, C$_{1-6}$alkoxy and halo substituted-C$_{1-6}$alkyl or -C$_{1-6}$alkoxy; and any alkyl group of R$_1$ can optionally have a methylene replaced by an atom or group chosen from —S—, —S(O)—, —S(O)$_2$—, —NR$_5$— and —O—; wherein R$_5$ is chosen from hydrogen or C$_{1-6}$alkyl;

R$_2$ is H, C$_{1-6}$alkyl, halo substituted C$_{1-6}$alkyl, C$_{2-6}$alkenyl or C$_{2-6}$alkynyl: and each of R$_3$ or R$_4$, independently, is H, halogen, OH, C$_{1-6}$alkyl, C$_{1-6}$alkoxy or halo substituted C$_{1-6}$alkyl or C$_{1-6}$alkoxy;

and the N-oxide derivatives thereof or prodrugs thereof, individual isomers and mixtures of isomers thereof; and the pharmacologically acceptable salts, solvates or hydrates thereof. For these compounds of Formula Ia or Ib, in one embodiment R$_1$ is phenyl, naphthyl or thienyl optionally substituted by C$_{6-10}$aryl, C$_{6-10}$aryl, C$_{1-4}$alkyl, C$_{2-9}$heteroaryl, C$_{2-9}$heteroarylC$_{1-4}$alkyl, C$_{3-8}$cycloalkyl, C$_{3-8}$cycloalkylC$_{1-4}$alkyl, C$_{3-8}$heterocycloalkyl, C$_{3-8}$heterocycloalkylC$_{1-4}$alkyl or C$_{1-6}$alkyl; wherein any aryl, heteroaryl, cycloalkyl or heterocycloalkyl group of R$_1$ can be optionally substituted by one to five radicals chosen from halo, C$_{1-6}$alkyl, C$_{1-6}$alkoxy, halo-substituted-C$_{1-6}$alkyl and halo-substituted-C$_{1-6}$alkoxy; and any alkyl group of R$_1$ can optionally have a methylene replaced by an atom or group chosen from —S—, —S(O)—, —S(O)$_2$—, —NR$_5$— and —O—; wherein R$_5$ is hydrogen or C$_{1-6}$alkyl.

In another embodiment, Y is chosen from:

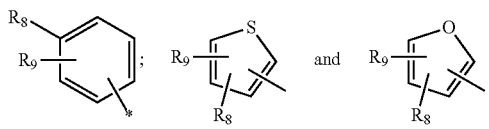

wherein R$_7$ is hydrogen or C$_{1-6}$alkyl; and the left and right asterisks of Y indicate the point of attachment a) either between —C(R$_2$)=NOWR$_1$ and the —CR$_3$R$_4$—, or between —CR$_3$R$_4$— and —C(R$_2$)=NOWR$_1$ of Formula Ia, respectively, or b) either between —CR$_3$R$_4$— and W or between W and —CR$_3$R$_4$— of Formula Ib, respectively; wherein any aryl or heteroaryl of Y can be optionally substituted with 1 to 3 radicals chosen from halo, hydroxy, nitro, C$_{1-6}$alkyl, C$_{1-6}$alkoxy, halo-substituted C$_{1-6}$alkyl and halo-substituted C$_{1-6}$alkoxy.

In a further embodiment, R$_1$ is chosen from:

wherein the asterisk is the point of attachment of R$_1$ with W; R$_8$ is C$_{6-10}$aryl, C$_{6-10}$arylC$_{1-4}$alkyl, C$_{2-9}$heteroaryl, C$_{2-9}$heteroarylC$_{1-4}$alkyl, C$_{3-8}$cycloalkyl, C$_{3-8}$cycloalkyl C$_{1-4}$alkyl, C$_{3-8}$heterocycloalkyl, C$_{3-8}$heterocycloalkyl-C$_{1-4}$alkyl or C$_{1-6}$alkyl; wherein any aryl, heteroaryl, cycloalkyl or heterocycloalkyl group of R$_8$ can be optionally substituted by one to three radicals chosen from halo, C$_{1-6}$alkyl, C$_{1-6}$alkoxy, halo-substituted-C$_{1-6}$alkyl and halo-substituted-C$_{1-6}$alkoxy; and any alkyl group of R$_8$ can optionally have a methylene replaced by an atom or group chosen from —S—, —S(O)—, —S(O)$_2$—, —NR$_5$— and —O—; wherein R$_5$ is hydrogen or C$_{1-6}$alkyl; and R$_9$ is chosen from halo, C$_{1-6}$alkyl, C$_{1-6}$alkoxy, halo-substituted-C$_{1-6}$alkyl and halo-substituted-C$_{1-6}$alkoxy.

In another embodiment, A is —C(O)OH; and Z is chosen from:

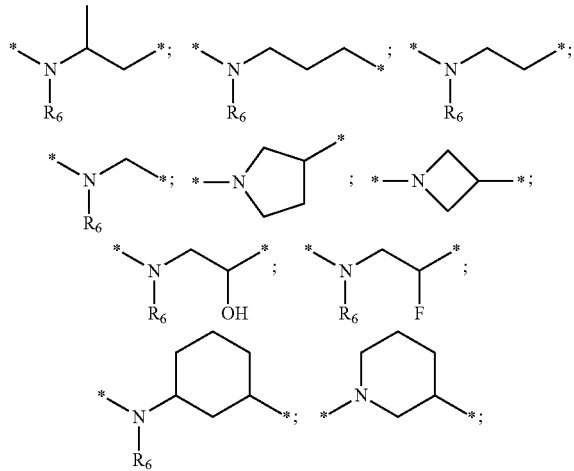

wherein the left and right asterisks of Z indicate the point of attachment between —C(R$_3$)(R$_4$)— and A of Formula Ia or Ib, respectively; R$_6$ is chosen from hydrogen and C$_{1-6}$alkyl; and R$_3$ and R$_4$ are both hydrogen.

In a further embodiment, Y is chosen from phenyl, pyridinyl, thienyl and furanyl; wherein any phenyl, pyridinyl, thienyl or furanyl of Y is optionally substituted with 1 to 3 radicals chosen from methyl, ethyl, cyclopropyl, chloro, bromo, fluoro and methoxy; or where Y is phenyl, R$_6$ can be attached to a carbon atom of Y to form 3,4-dihydro-1H-isoquinolin-2-yl.

In another embodiment, W is a bond or methylene; R$_1$ is chosen from:

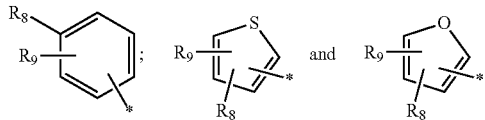

wherein R$_8$ is chosen from phenyl, cyclohexyl, thienyl, 3,3-dimethyl-butyl, pyridinyl, cyclopentyl and piperidinyl; wherein R$_8$ can be optionally substituted by 1 to 3 radicals chosen from trifluoromethyl, methoxy, fluoro, trifluoromethoxy and methyl; and R$_9$ is chosen from trifluoromethyl, fluoro, methyl, chloro, methoxy and ethyl.

Preferred compounds of the invention include: 3-{4-[1-(2-Trifluoromethyl-biphenyl-4-ylmethoxyimino)-ethyl]-benzylamino}-propionic acid, 3-{4-[1-(4-Cyclohexyl-3-trifluoromethyl-benzyloxyimino)-ethyl]-2-ethyl-benzylamino}-propionic acid, 1-{4-[1-(4-Cyclohexyl-3-trifluoromethyl-benzyloxyimino)-ethyl]-2-ethyl-benzyl}-azetidine-3-carboxylic acid, 3-({2-Chloro-6-[1-(4-cyclohexyl-3-trifluoromethyl-benzyloxyimino)-ethyl]-pyridin-3-ylmethyl}-amino)-propionic acid, 3-({6-[1-(4-Cyclohexyl-3-trifluoromethyl-benzyloxyimino)-ethyl]-2-ethyl-pyridin-3-ylmethyl}-amino)-propionic acid, 3-{4-[1-(Biphenyl-4-ylmethoxyimino)-ethyl]-benzylamino}-propionic acid, 4-{4-[1-(Biphenyl-4-ylmethoxyimino)-ethyl]-benzylamino}-butyric acid, 1-{4-[1-(Biphenyl-4-ylmethoxyimino)-ethyl]-benzyl}-azetidine-3-carboxylic acid, 1-{4-[1-(Biphenyl-4-ylmethoxyimino)-ethyl]-benzyl}-piperidine-3-carboxylic acid, {4-[1-(Biphenyl-4-ylmethoxyimino)-ethyl]-benzylamino}-acetic acid, 3-{4-[1-(Biphenyl-4-ylmethoxyimino)-ethyl]-benzylamino}-cyclopentanecarboxylic acid, 3-{4-[1-(4'-Trifluoromethyl-biphenyl-4-ylmethoxyimino)-ethyl]-benzylamino}-propionic acid, 3-{4-[1-(5-Phenyl-furan-2-ylmethoxyimino)-ethyl]-benzylamino}-propionic acid, 3-{-4-[1-(3'-Trifluoromethyl-biphenyl-4-ylmethoxyimino)-ethyl]-benzylamino}-propionic acid, 3-{-4-[1-(3-Trifluoromethyl-biphenyl-4-ylmethoxyimino)-ethyl]-benzylamino}-propionic acid, 3-{-4-[1-(4'-Methoxy-biphenyl-4-ylmethoxyimino)-ethyl]-benzylamino}-propionic acid, 3-{-4-[1-(Biphenyl-3-ylmethoxyimino)-ethyl]-benzylamino}-propionic acid, 3-{4-[1-(4-Thiophen-2-yl-benzyloxyimino)-ethyl]-benzylamino}-propionic acid, 3-{4-[1-(4-Thiophen-2-yl-3-trifluoromethyl-benzyloxyimino)-ethyl]-benzylamino}-propionic acid, 3-{4-[1-(4'-Fluoro-biphenyl-4-ylmethoxyimino)-ethyl]-benzylamino}-propionic acid, 3-{4-[1-(4'-Trifluoromethoxy-biphenyl-4-ylmethoxyimino)-ethyl]-benzylamino}-propionic acid, 3-{4-[1-(3'-Trifluoromethoxy-biphenyl-4-ylmethoxyimino)-ethyl]-benzylamino}-propionic acid, 1-{4-[1-(2-Trifluoromethyl-biphenyl-4-ylmethoxyimino)-ethyl]-benzyl}-azetidine-3-carboxylic acid, 1-{4-[1-(2-Trifluoromethyl-biphenyl-4-ylmethoxyimino)-ethyl]-benzyl}-pyrrolidine-3-carboxylic acid, 1-{4-[1-(2-Trifluoromethyl-biphenyl-4-ylmethoxyimino)-ethyl]-benzyl}-piperidine-3-carboxylic acid, 3-{4-[1-(3'-Methoxy-biphenyl-4-ylmethoxyimino)-ethyl]-benzylamino}-propionic acid, 2-Hydroxy-3-{4-[1-(2-trifluoromethyl-biphenyl-4-ylmethoxyimino)-ethyl]-benzylamino}-propionic acid, 3-{4-[1-(4'-Methyl-biphenyl-4-ylmethoxyimino)-ethyl]-benzylamino}-propionic acid, 3-{4-[1-(4-Phenyl-thiophen-2-ylmethoxyimino)-ethyl]-benzylamino}-propionic acid, 1-{4-[1-(Biphenyl-4-ylmethoxyimino)-ethyl]-benzyl}-pyrrolidine-3-carboxylic acid, 3-{4-[1-(4-Furan-3-yl-benzyloxyimino)-ethyl]-benzylamino}-propionic acid, 3-{4-[1-(4-Thiophen-3-yl-3-trifluoromethyl-benzyloxyimino)-ethyl]-benzylamino}-propionic acid, 3-{4-[1-(4-Thiophen-3-yl-2-trifluoromethyl-benzyloxyimino)-ethyl]-benzylamino}-propionic acid, 2-Fluoro-3-{4-[1-(2-trifluoromethyl-biphenyl-4-ylmethoxyimino)-ethyl]-benzylamino}-propionic acid, 3-{4-[1-(2-Trifluoromethyl-biphenyl-4-ylmethoxyimino)-ethyl]-benzylamino}-butyric acid, 3-{4-[1-(5-Phenyl-thiophen-2-ylmethoxyimino)-ethyl]-benzylamino}-propionic acid, 3-{4-[1-(4-Cyclohexyl-benzyloxyimino)-ethyl]-benzylamino}-propionic acid, 3-{4-[1-(3-Fluoro-biphenyl-4-ylmethoxyimino)-ethyl]-benzylamino}-propionic acid, 3-{4-[1-(4'-Fluoro-2-trifluoromethyl-biphenyl-4-ylmethoxyimino)-ethyl]-benzylamino}-propionic acid, 3-{4-[1-(4'-Methyl-2-trifluoromethyl-biphenyl-4-ylmethoxyimino)-ethyl]-benzylamino}-propionic acid, 3-{4-[1-(4-Furan-2-yl-3-trifluoromethyl-benzyloxyimino)-ethyl]-benzylamino}-propionic acid, 3-{4-[1-(2'-Fluoro-2-trifluoromethyl-biphenyl-4-ylmethoxyimino)-ethyl]-benzylamino}-propionic acid, 3-(4-{1-[4-(3,3-Dimethyl-butyl)-3-trifluoromethyl-benzyloxyimino]-ethyl}-benzylamino)-propionic acid, 3-{4-[1-(4-Furan-3-yl-3-trifluoromethyl-benzyloxyimino)-ethyl]-benzylamino}-propionic acid, 3-{4-[1-(4-Pyridin-3-yl-benzyloxyimino)-ethyl]-benzylamino}-propionic acid, 3-{4-[1-(4-Pyridin-4-yl-benzyloxyimino)-ethyl]-benzylamino}-propionic acid, 3-{4-[1-(2-Fluoro-biphenyl-4-ylmethoxyimino)-ethyl]-benzylamino}-propionic acid, 3-({2-Methoxy-6-[1-(2-trifluoromethyl-biphenyl-4-ylmethoxyimino)-ethyl]-pyridin-3-ylmethyl}-amino)-propionic acid, 3-{4-[1-(4-Cyclohexyl-3-trifluoromethyl-benzyloxyimino)-ethyl]-2-ethyl-benzylamino}-propionic acid, 3-{4-[1-(4-Cyclohexyl-3-trifluoromethyl-benzyloxyimino)-ethyl]-benzylamino}-propionic acid, 3-{2-Bromo-4-[1-(4-cyclohexyl-3-trifluoromethyl-benzyloxyimino)-ethyl]-benzylamino}-propionic acid, 3-{4-[1-(4-Cyclopentyl-3-trifluoromethyl-benzyloxyimino)-ethyl]-benzylamino}-propionic acid, 3-{2-Chloro-4-[1-(4-cyclohexyl-3-trifluoromethyl-benzyloxyimino)-ethyl]-benzylamino}-propionic acid, 3-({6-[1-(4-Cyclohexyl-3-trifluoromethyl-benzyloxyimino)-ethyl]-pyridin-3-ylmethyl}-amino)-propionic acid, 3-({5-[1-(4-Cyclohexyl-3-trifluoromethyl-benzyloxyimino)-ethyl]-thiophen-2-ylmethyl}-amino)-propionic acid, 3-({5-[1-(4-Cyclohexyl-3-trifluoromethyl-benzyloxyimino)-ethyl]-pyridin-2-ylmethyl}-amino)-propionic acid, 3-({5-[1-(4-Cyclohexyl-3-trifluoromethyl-benzyloxyimino)-ethyl]-furan-2-ylmethyl}-amino)-propionic acid, 3-({2-[1-(4-Cyclohexyl-3-trifluoromethyl-benzyloxyimino)-ethyl]-pyridin-4-ylmethyl}-amino)-propionic acid, 3-{4-[1-(4-Cyclohexyl-3-fluoro-benzyloxyimino)-ethyl]-benzylamino}-propionic acid, 3-{2-Chloro-4-[1-(4-cyclohexyl-3-trifluoromethyl-benzyloxyimino)-ethyl]-benzylamino}-propionic acid, 1-{6-[1-(4-Cyclohexyl-3-trifluoromethyl-benzyloxyimino)-ethyl]-2-ethyl-pyridin-3-ylmethyl}-azetidine-3-carboxylic acid, 3-{2-Ethyl-4-[1-(4-piperidin-1-yl-3-trifluoromethyl-benzyloxyimino)-ethyl]-benzylamino}-propionic acid, 3-{4-[1-(4-Cyclohexyl-3-methyl-benzyloxyimino)-ethyl]-2-ethyl-benzylamino}-propionic acid, 3-{4-[1-(3-Chloro-4-cyclohexyl-benzyloxyimino)-ethyl]-2-ethyl-benzylamino}-propionic acid, 3-{4-[1-(4-Cyclohexyl-3-methoxy-benzyloxyimino)-ethyl]-2-ethyl-benzylamino}-propionic acid, 1-{4-[1-(4-Cyclohexyl-3-methoxy-benzyloxyimino)-ethyl]-2-ethyl-benzyl}-azetidine-3-carboxylic acid, 3-{4-[1-(4-Cyclohexyl-3-trifluoromethyl-benzyloxyimino)-ethyl]-2-methyl-benzylamino}-propionic acid, 1-{4-[1-(4-Cyclohexyl-3-trifluoromethyl-benzyloxyimino)-ethyl]-2-methyl-benzyl}-azetidine-3-carboxylic acid, 3-{4-[1-(4-Cyclohexyl-3-trifluoromethyl-benzyloxyimino)-ethyl]-2-cyclopropyl-benzylamino}-propionic acid, 1-{4-[1-(4-Cyclohexyl-3-trifluoromethyl-benzyloxyimino)-ethyl]-2-cyclopropyl-benzyl}-azetidine-3-carboxylic acid, 3-{2-Ethyl-4-[1-(2-trifluoromethyl-biphenyl-4-ylmethoxyimino)-ethyl]-benzylamino}-propionic acid, 1-{4-[1-(4-Cyclohexyl-3-ethyl-benzyloxyimino)-ethyl]-2-ethyl-benzyl}-azetidine-3-carboxylic acid, 1-{4-[1-(4-Cyclohexyl-3-methyl-benzyloxyimino)-ethyl]-2-ethyl-benzyl}-azetidine-3-carboxylic acid, 1-{2-Chloro-4-[1-(4-cyclohexyl-3-ethyl-benzyloxyimino)-ethyl]-benzyl}-azetidine-3-carboxylic acid, 3-{2-Chloro-4-[1-(4-cyclohexyl-3-ethyl-benzyloxyimino)-ethyl]-benzylamino}-propionic acid, 3-{4-[1-(4-Cyclohexyl-3-trifluoromethyl-benzyloxyimino)-ethyl]-2-fluoro-benzylamino}-propionic acid, 1-{4-[1-(4-Cyclohexyl-3-trifluoromethyl-benzyloxyimino)-ethyl]-2-fluoro-benzyl}-azetidine-3-carboxylic acid, 3-{6-[1-(4-Cyclohexyl-3-trifluoromethyl-benzyloxyimino)-ethyl]-3,4-dihydro-1H-isoquinolin-2-yl}-propionic acid, 3-{6-[1-(4-Cyclohexyl-3-ethyl-benzyloxyimino)-ethyl]-3,4-dihydro-1H-isoquinolin-2-yl}-propionic acid, 3-{4-[1-(2-Trifluoromethyl-biphenyl-4-yl)-ethylideneaminooxymethyl]-benzylamino}-propionic acid, 3-{4-[1-(4-Cyclohexyl-3-trifluoromethyl-phenyl)-ethylideneaminooxymethyl]-benzylamino}-propionic acid, 3-{4-[1-(4-Cyclohexyl-3-trifluoromethyl-phenyl)-ethylideneaminooxymethyl]-2-ethyl-benzylamino}-propionic acid, 1-{4-[1-(4-Cyclohexyl-3-trifluoromethyl-phenyl)-ethylideneaminooxymethyl]-2-ethyl-benzyl}-azetidine-3-carboxylic acid and 1-{4-[1-(4-Cyclohexyl-3-ethyl-phenyl)-ethylideneaminooxymethyl]-2-ethyl-benzyl}-azetidine-3-carboxylic acid.

The invention provides forms of the compound that have the hydroxyl or amine group present in a protected form; these function as prodrugs. Prodrugs are compounds that are converted into an active drug form after administration, through one or more chemical or biochemical transformations. Forms of the compounds of the present invention that are readily converted into the claimed compound under physiological conditions are prodrugs of the claimed compounds and are within the scope of the present invention. Examples of prodrugs include forms where a hydroxyl group is acylated to form a relatively labile ester such as an acetate ester, and forms where an amine group is acylated with the carboxylate group of glycine or an L-amino acid such as serine, forming an amide bond that is particularly susceptible to hydrolysis by common metabolic enzymes.

When the compounds of Formula Ia or Ib have asymmetric centers in the molecule, various optical isomers are obtained. The present invention also encompasses enantiomers, racemates, diastereoisomers and mixtures thereof. Moreover, when the compounds of Formula Ia or Ib include geometric isomers, the present invention embraces cis-compounds, trans-compounds and mixtures thereof. Similar considerations apply in relation to starting materials exhibiting asymmetric carbon atoms or unsaturated bonds as mentioned above. Compounds of Formula Ia or Ib can exist in free form or in salt form, e.g. addition salts with inorganic or organic acids. Where hydroxyl groups are present, these groups can also be present in salt form, e.g. an ammonium salt or salts with metals such as lithium, sodium, potassium, calcium, zinc or magnesium, or a mixture thereof. Compounds of Formula Ia or Ib and their salts in hydrate or solvate form are also part of the invention.

A preferred compound of formula Ia is e.g. 1-{4-[1-(4-cyclohexyl-3-trifluoromethyl-benzyloxyimino)-ethyl]-2-ethyl-benzyl}-azetidine-3-carboxylic acid (Compound A), or a pharmaceutically acceptable salt or prodrug thereof.

Unless otherwise stated, alkyl, alkoxy, alkenyl or alkynyl may be straight or branched.

Halo or halogen means F, Cl, Br or I, preferably F or Cl. Halo-substituted alkyl groups and compounds can be partially halogenated or perhalogenated, whereby in the case of multiple halogenation, the halogen substituents can be identical or different. A preferred perhalogenated alkyl group is for example trifluoromethyl or trifluoromethoxy.

Any double bonds can be in the cis- or trans-configuration. "Alkynyl" as a group and as structural element of other groups and compounds contains at least one C≡C triple bond and can also contain one or more C═C double bonds, and can, so far as possible, be either straight-chain or branched. Any cycloalkyl group, alone or as a structural element of other groups can contain from 3 to 8 carbon atoms, preferably from 3 to 6 carbon atoms. "Alkylene" and "alkenylene" are divalent radicals derived from "alkyl" and "alkenyl" groups, respectively. In this application, any alkyl group of $R_1$ can be optionally interrupted by a member of the group selected from —S—, —S(O)—, —S(O)$_2$—, —NR$^{20}$— and —O— (wherein R$^{20}$ is hydrogen or $C_{1-6}$alkyl). These groups include —CH$_2$—O—CH$_2$—, —CH$_2$—S(O)$_2$—CH$_2$—, —(CH$_2$)$_2$—NR$^{20}$—CH$_2$—, —CH$_2$—O—(CH$_2$)$_2$—, and the like.

"Aryl" means a monocyclic or fused bicyclic aromatic ring assembly containing six to ten ring carbon atoms. For example aryl, e.g. $C_{6-10}$aryl, can be phenyl, biphenyl or naphthyl, such as phenyl or naphthyl, preferably phenyl. A fused bicyclic ring can be partially saturated, for example, 1,2,3,4-tetrahydro-naphthalene, and the like.

"Heteroaryl" means aryl, as defined in this application, with the addition of at least one heteroatom moiety selected from N, O or S, and each ring is comprised of 5 to 6 ring atoms, unless otherwise stated. For example, $C_2$heteroaryl includes oxadiazole, triazole, and the like. $C_9$heteroaryl includes quinoline, 1,2,3,4-tetrahydro-quinoline, and the like. $C_{2-9}$heteroaryl as used in this application includes thienyl, pyridinyl, furanyl, isoxazolyl, benzoxazolyl or benzo[1,3]dioxolyl, preferably thienyl, furanyl or pyridinyl. A fused bicyclic heteroaryl ring system can be partially saturated, for example, 2,3-dihydro-1H-isoindole, 1,2,3,4-tetrahydro-quinoline, and the like.

According to the invention, inflammatory myopathies include, but are not limited to muscle inflammations, polymyositis, dermatomyositis, nerve-muscle diseases such as muscular dystrophies, and inclusion body myositis (IBM).

It has now been found that the S1P receptor modulators of the invention have an inhibitory effect on inflammatory myopathies, e.g. polymyositis.

In a series of further specific or alternative embodiments, the present invention provides:

1.1 A method for preventing, inhibiting or treating muscle inflammation or inflammatory myopathies, e.g. polymyositis, in a subject in need thereof, comprising administering to said subject a therapeutically effective amount of a S1P receptor modulator of the invention modulator, e.g. a compound of formulae Ia or Ib, e.g. Compound A.

1.2 A method for alleviating or delaying progression of the symptoms of an inflammatory myopathy, e.g. polymyositis, in a subject in need thereof, in which method muscle inflammation associated with said disease is prevented or inhibited, comprising administering to said subject a therapeutically effective amount of a S1P receptor modulator of the invention, e.g. a compound of formulae Ia or Ib, e.g. Compound A.

1.3 A method for reducing or preventing or alleviating relapses in an inflammatory myopathy, e.g. polymyositis, in a subject in need thereof, in which method muscle inflammation associated with said disease is prevented or inhibited, comprising administering to said subject a therapeutically effective amount of a S1P receptor modulator of the invention, e.g. a compound of formulae Ia or Ib, e.g. Compound A.

1.4 A method for slowing progression of an inflammatory myopathy, e.g. polymyositis, in a subject being in a relapsing-remitting phase of the disease, in which method muscle inflammation associated with said disease is prevented or inhibited, comprising administering to said subject a therapeutically effective amount of a S1P receptor modulator of the invention modulator, e.g. a compound of formulae I or Ib, e.g. Compound A.

2. A pharmaceutical composition for use in any one of the methods 1.1 to 1.5, comprising a S1P receptor modulator of the invention, e.g. a compound of formulae Ia or Ib, e.g. Compound A, as defined hereinabove, together with one or more pharmaceutically acceptable diluents or carriers therefor.

3. A S1P receptor modulator of the invention, e.g. a compound of formula Ia or Ib, e.g. Compound A, as defined herein above, for use in any one of the methods 1.1 to 1.5.

4. A S1P receptor modulator of the invention, e.g. a compound of formula Ia or Ib, e.g. Compound A, as defined herein above, for use in the preparation of a medicament for use in any one of the methods 1.1 to 1.5.

5. Use of a S1P receptor modulator of the invention, e.g. a compound of formula Ia or Ib, e.g. Compound A as defined herein above, in any one of the methods 1.1 to 1.5 e.g. 1.1.

6. Use of a S1P receptor modulator of the invention, e.g. a compound of formulae Ia or Ib, e.g. Compound A as defined herein above, in the preparation of a medicament for use in a method according to one of the methods 1.1 to 1.5 e.g. 1.1.

7. A method, use, or pharmaceutical composition according to any one of the preceding paragraphs 1.1-1.5 and 2-6 wherein the S1P receptor modulator of the invention is 1-{4-[1-(4-cyclohexyl-3-trifluoromethyl-benzyloxyimino)-ethyl]-2-ethyl-benzyl}-azetidine-3-carboxylic acid in free form or in a pharmaceutically acceptable salt form.

Administration

Daily dosages required in practicing the method of the present invention when a S1P receptor modulator of the invention alone is used will vary depending upon, for example, the compound used, the host, the mode of administration and the severity of the condition to be treated. A preferred daily dosage range is about from 0.01 to 100 mg as a single dose or in divided doses. Suitable daily dosages for patients are on the order of from e.g. 0.03 to 2.5 mg/kg per body weight. The S1P receptor modulators of the invention may be administered by any conventional route, in particular enterally, e.g. orally, e.g. in the form of tablets, capsules, parenterally, e.g. in the form of injectable solutions or suspensions, or topically, e.g. in the form of lotions, gels, ointments or creams, or in a nasal or a suppository form. Suitable unit dosage forms for oral administration comprise from ca. 0.5 to about 100 mg, e.g. 1 to 50 mg S1P receptor modulator of the invention, together with one or more pharmaceutically acceptable diluents or carriers therefore.

The compounds of Formula Ia or Ib may be administered as the sole active ingredient or in conjunction with, e.g. as an adjuvant to, other drugs e.g. immunosuppressive or immunomodulating agents or other anti-inflammatory agents. For example the compounds of Formula Ia or Ib may be used in combination with a calcineurin inhibitor, e.g. cyclosporin A or FK 506; an ascomycin having immunosuppressive properties, e.g. ABT-281, ASM981, etc.; corticosteroids; cyclophosphamide; azathioprene; methotrexate; leflunomide; mizoribine; mycophenolic acid; mycophenolate mofetil; 15-deoxyspergualine or an immunosuppressive homologue, analogue or derivative thereof; immunosuppressive monoclonal antibodies, e.g. monoclonal antibodies to leukocyte receptors, e.g. MHC, CD2, CD3, CD4, CD7, CD8, CD25, CD28, CD40. CD45, CD58, CD80, CD86 or their ligands; other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4Ig (for ex. designated ATCC 68629) or a mutant thereof, e.g. LEA29Y; adhesion molecule inhibitors, e.g. LFA-1 antagonists, ICAM-1 or -3 antagonists, VCAM-4 antagonists or VLA-4 antagonists.

METHODS OF PREPARING THE COMPOUNDS FOR USE IN THE INVENTION

The compounds for use in the aspects of the invention may, for example, be prepared by the methods specified in WO 2004/103306.

EXAMPLES

Utility of the S1P receptor modulators of the invention, e.g. 1-{4-[1-(4-cyclohexyl-3-trifluoromethyl-benzyloxyimino)-ethyl]-2-ethyl-benzyl}-azetidine-3-carboxylic acid (Compound A), in preventing or treating an inflammatory myopathy, e.g. polymyositis, as hereinabove specified, may be demonstrated in vitro, in animal test methods as well as in clinic, for example in accordance with the methods hereinafter described.

In Vitro: Effect on Cytokine-Induced Atrophy of Primary Human Myotubes.

Human skeletal muscle (skMC) cells are obtained from Cambrex (#CC-2561). For experiments skMC stocks are thawed and maintained in SkBM (Lonza CC-3161) containing 20% FCS and 0.1% gentamycin at 37° C., 5% $CO_2$. After 4-5 days cells are seeded for experiments onto six-well plates coated with matrigel (450,000/well) and grown at 37° C., 5% $CO_2$ for one day. Cells are then washed 3× with SkBM and differentiated into myotubes with SkBM containing 1 μM SB431542 (ALK4/5 inhibitor; Sigma #S4317) for 4 days (SB431542 is removed 24 h prior cell treatment). Myotubes are then treated with test compound either in the absence or in the presence of a cytokine cocktail (TNFα 10 ng/ml, IL-1β 2 ng/ml, IFNγ 10 ng/ml) for 24 h in SkBM plus 0.1% gentamycin, washed once with CSB buffer: 80 mM pipes, 5 nM EGTA, 1 mM MgCl 6H$_2$0 and 4% PEG35000 (Fluka #94646) and fixed with 4% paraformaldehyde (Electron Microscopy Sciences #15714) in CSB for 15 min at room temperature. Cells are then rinsed with CSB, permeabilized with 0.2% Triton X-100 (Merk #1.12298.0100) for 20 min at room temperature, rinsed with CSB and blocked with 10% normal goat serum blocking solution (Zymed Laboratories #50-062Z) for 20 min at room temperature. Primary antibody (anti-myosin heavy chain antibody; Upstate #05-716) diluted 1:500 in PBS containing 1.5% goat serum is added for 1 h at room temperature. Myotubes are then washed 2× with CSB (5 min/wash) then add secondary antibody (Alexa Fluor 488 F(ab'); Invitrogen #A11017) diluted 1:750 in PBS is added for 1 h at room temperature. Myotubes are washed once with CSB (10 min) then with PBS (Invitrogen #14190) and double distilled water. Finally, ProLong Gold antifade reagent with DAPI (Invitrogen #P36931) is added and myotubes are photographed. Average diameters of at least 40 myotubes are measured for each condition at three points separated by 50 μm along the length of the myotube.

Figure 1B:
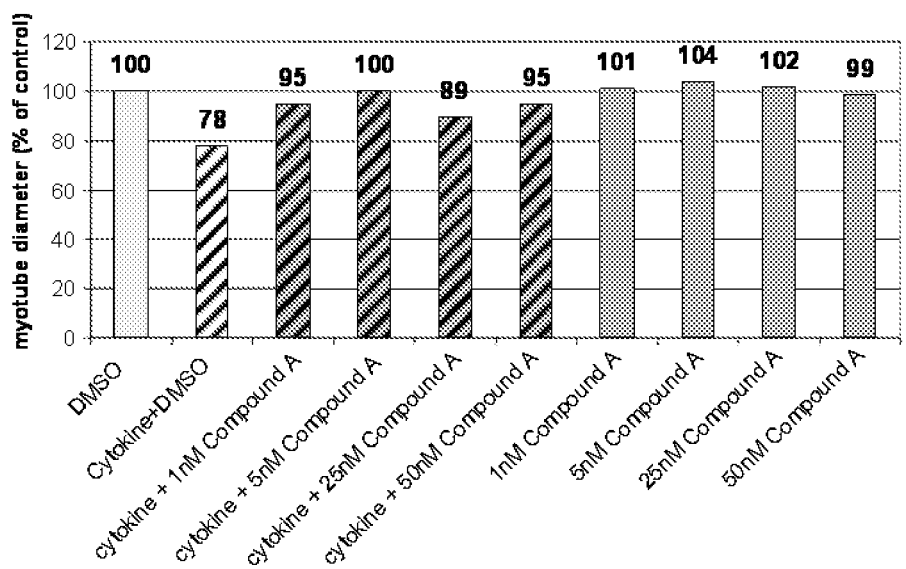

Human primary myoblasts, differentiated for 4 days and treated with cytokine cocktail for 24 h, fixed, and assayed for changes in myotube diameters show distinct atrophic phenotype with an approx. 20% decrease in myotube diameter as compared to vehicle control. Addition of Compound A at a concentration of 1 nM is sufficient to block almost completely the cytokine-induced atrophy. Higher concentrations of Compound A exert the same effect. The results are shown in FIGS. 1(a) and 1(b).

In vivo: controllable muscle-specific promoter system to up-regulate MHC class I in the skeletal muscle of mice, as described e.g. in K. Nagaraju et al (PNAS, Aug. 1, 2000, Vol 97, No. 16, p 9209-9214), the content thereof being included by reference.

Briefly, mice transgenic for both a transactivator (tTA) under the control of a muscle creatine kinase promoter (T$^+$) and the tetracycline-responsive element (TRE)-H-2K$^b$ (H$^+$) are used. In H$^+$T$^+$ mice, the binding of a tetracycline analog to tTA prevents transactivator from binding to the TRE region, thereby preventing target gene expression. Thus, the transgenic H-2K$^b$ expression can be induced by removing the tetracycline analog and suppressed by administering it. Mice having only the tetracycline-responsive element (TRE)-H-2Kb (H$^+$) serve as control. H$^+$T$^+$ mice develop clinical, biochemical, histological, and immunological features similar to human myositis. First signs of disease are muscle weakness (about 3 months of age in females, i.e. 2 months after transgene induction).

Behavioral assays are used to measure developing muscle weakness (e.g. treadmill, RotaRod, open field locomotor activity, running wheel, grip test). Other readouts of the model include blood markers indicative for muscle damage (CK, GOT etc.), and histopathology and immunohistochemistry of skeletal muscle (incl. mononuclear cell infiltrate, CD3$^+$ T cell infiltrate, ICAM, etc.).

Application of compound in the therapeutic mode may start around 3 months of age in female mice (2 month after transgene induction), when first clinical signs of muscle weakness occur and may last e.g. for 2 months. Compounds are applied i.p., s.c. or via sirup drops into the mouth. Oral gavage is not recommended due to dystrophy of pharyngeal muscles. Groups of n=8 mice are used. Compounds are applied to mice having both transgenes, H$^+$T$^+$ and mice having only the tetracycline-responsive element (TRE)-H-2Kb (H$^+$, control). Vehicle-treated animals are compared to compound-treated animals.

Application of compound in the prophylactic mode starts from day of transgene induction. Both, therapeutic and prophylactic treatment mode can be combined with other therapeutics, like e.g. prednisone or comparable steroids.

The invention claimed is:

1. A method for treating polymyositis in a subject in need thereof, comprising administering to said subject a therapeutically effective amount of 1-{4-[1-(4-cyclohexyl-3-trifluoromethyl-benzyloxyimino)-ethyl]-2-ethyl-benzyl}-azetidine-3-carboxylic acid or an N-oxide derivative thereof, a prodrug thereof, an individual isomer or mixtures of isomers thereof; or a pharmacologically acceptable salt, solvate or hydrate thereof.

* * * * *